United States Patent [19]

Dahl et al.

[11] Patent Number: 5,020,544

[45] Date of Patent: Jun. 4, 1991

[54] LOW ENERGY DEFIBRILLATION ELECTRODE

[75] Inventors: Roger W. Dahl, Andover; Ronald W. Heil, Jr., Roseville; Graydon E. Beatty, New Brighton, all of Minn.; Morton M. Mower, Lutherville, Md.

[73] Assignee: Cardiac Pacemakers, Inc., St. Paul, Minn.

[21] Appl. No.: 430,050

[22] Filed: Nov. 1, 1989

[51] Int. Cl.⁵ ............................................. A61N 1/05
[52] U.S. Cl. ................................... 128/784; 128/798; 128/419 D
[58] Field of Search ............ 128/784, 785, 798, 419 D

[56] References Cited

U.S. PATENT DOCUMENTS

| | | | |
|---|---|---|---|
| 2,985,172 | 5/1961 | Jones | 128/784 |
| 4,291,707 | 9/1981 | Heilman et al. | 128/784 |
| 4,444,206 | 4/1984 | Gold | 128/784 |
| 4,548,203 | 10/1985 | Tacker, Jr. et al. | 128/784 X |
| 4,567,900 | 2/1986 | Moore | 128/784 |
| 4,711,251 | 12/1987 | Stokes | 128/784 |
| 4,765,341 | 8/1988 | Mower | 128/785 |
| 4,817,634 | 4/1989 | Holleman et al. | 128/784 |
| 4,827,932 | 5/1989 | Ideker et al. | 128/419 D |

FOREIGN PATENT DOCUMENTS

| | | | |
|---|---|---|---|
| 0057451 | 8/1982 | European Pat. Off. | 128/785 |
| 2182566 | 5/1987 | United Kingdom | 128/784 |

*Primary Examiner*—Lee S. Cohen
*Attorney, Agent, or Firm*—Fleit, Jacobson, Cohn, Price, Holman & Stern

[57] ABSTRACT

An implantable cardiac electrode for use in defibrillation. The electrode comprises a plurality of layers of porous conductive screens and backed by an insulation layer. When implanted on or about the heart surface, body fluids can flow through the screens thus increasing the effective surface area of contact. Each individual layer of mesh can be microscopically textured to create indentations on the layer for further increasing the surface area of each screen, and thus, the surface area of body fluid contact. Also disclosed is an electrode without an insulative backing facing away from the heart.

38 Claims, 2 Drawing Sheets

LOW ENERGY DEFIBRILLATION ELECTRODE

BACKGROUND OF THE INVENTION

This invention relates to an electrode for medical applications, particularly an implantable defibrillation electrode.

Electrodes implanted in the body for electrical defibrillation are well known. More specifically, electrodes implanted on or about the heart have been used to reverse (i.e., defibrillate or cardiovert) certain life-threatening cardiac arrhythmias by applying electrical energy to the heart via these electrodes to return the heart to normal sinus rhythm. The amount of energy delivered to the heart during defibrillation (or cardioversion) depends on the placement of the electrodes on the heart and the ability of the electrode to distribute the energy applied as input to the electrodes through the heart. This energy is called the defibrillation or cardioversion energy.

In defibrillation, two opposing electrodes are typically implanted on or about the heart to create an electric field across and through the heart. This field eliminates the sporadic electrical impulses present throughout the heart that characterize fibrillation. Factors that determine the shape and strength of the field in the heart, and the efficiency with which the field is generated, are the shape of the electrodes, the amount of reactive surface area of the electrodes, the placements of the electrodes and the selection of the electrode materials. All of these factors have the effect of reducing the electrode interface impedance allowing the transfer of more energy to the heart tissue between the electrodes. All implantable devices have a finite amount of energy available making it imperative that discharge is delivered as efficiently as possible. This is particularly important when dealing with high energy (10–15 Joule) defibrillation shocks.

There have been attempts to develop desirable field shapes and discharge energies by the use of two electrodes in patch form placed in the region of the heart. See, for example, U.S. Pat. Nos. to Heilman et al. (4,030,509 and 4,291,707) and European Patent Application No. 0,280,564 to Ideker. Although such two patch electrode arrangements are effective, the electrodes may become so large or be placed so closely together that there is a danger of an electrical short-circuit or low impedance shunt developing between the two electrodes. Once that short develops, no effective electric field is generated and defibrillation cannot occur.

U.S. Pat. No. to Enger (4,011,861) discloses an implantable electrode having conductive porous layers formed into particular electrode shapes. The Enger device is described for use as a heart sensor or stimulator and comprises a disc of conductive porous material attached to a layer of inner non-absorbable conductive porous material. This porous structure is said to allow intermeshing with the tissue and permit ingress of blood vessels without the production of a fibrous tissue ingrowth interface. Moreover, it is stated that body electrolytes can fill the interstices of the porous layer to contact the electrically conductive source of the electrode.

U.S. Pat. No. to Cannon (3,981,309) discloses a stimulating pacing electrode of a cylindrical shape formed of a conductive porous material such as platinum dust. The patent contends that the resulting multiplicity of interstices provides a large surface area to reduce polarization losses and to facilitate small electrode dimensions for increasing the stimulation current density. Both the Enger and Cannon electrode designs are for use in pacemaker systems, not in higher energy defibrillation systems.

Other implantable electrodes are disclosed in U.S. Pat. Nos. to DeHaan et al. (4,649,937) and Hirshorn et al. (4,407,302). The DeHann et al. patent discloses an implantable electrode tip member having a plurality of grooves etched in the bullet shaped distal end. The patent purports that an enlarged surface area is created on a relatively small tip to ensure sufficient current flow into the organ tissue. The Hirshorn et al. patent discloses a cardiac pacemaker electrode tip structure having its external surface roughened by abrading with a jet of glass beads projected under pressure. This etching is stated to increase the microsurface area of the tip resulting in a decrease of the sensing impedance and an increase in the pacing impedance of the electrode. As a result, less current drain on the pacemaker power source is said to occur increase the life span of the pacemaker. While both patents describe methods to increase surface area, neither discusses the use of the increased surface area for direct blood/tissue contact in a defibrillation environment.

Further porous structures of implantable electrodes are discussed in the U.S. Pat. Nos. to Hirshorn et al. (4,408,604) and MacGregor (4,281,669). The MacGregor patent discloses a pacemaker electrode having a distal tip end formed of porous material to permit the formation of a smooth adherent tissue coating without the formation of blood clots. This electrode is said to achieve very high current density at several points on the surface while exerting a low energy drain from the battery. The Hirshorn et al. patent discloses a similar porous pacemaker electrode tip member which enables tissue to grow into the apertures to facilitate attachment to a body organ. In addition, it is stated in the patent that this structure provides a large microsurface area resulting in a low sensing impedance to improve sensing capability. Neither the Hirshorn et al. device nor the MacGregor device uses the porous structure to increase the surface contact area or to allow body fluids to enter the electrode. Also, neither of these electrodes are described as for use in implantable defibrillation systems.

U.S. Pat. Nos. to Mund et al. (4,603,704) and Parsonnet et al. (3,476,116) disclose pacemaker electrodes having means to provide direct blood contact with the electrical conductor of the electrode. The Mund et al. device comprises an elongated electrically conductive carrier material surrounded by porous layers. This porous system is said to provide a high double layer capacitance to keep the energy consumption low. The Parsonnet et al. device comprises a small container completely enclosed except for a small hole. Platinum foil is placed inside the container and connected to a pulse generator. The container is filled with saline solution or blood and placed in the body with the hole facing the heart surface. The patent states that all of the current on the foil must pass through the hole at a very high density with a substantial reduction of polarization effects. Both of these designs require intricate constructions and also are not applicable to defibrillation techniques.

Other attempts to lower pacing threshold energies through the use of drug elution are described in the U.S. Pat. Nos. to Stokes (4,506,680 and 4,577,642) and White (4,360,031).

SUMMARY OF THE INVENTION

The present invention relates to the field of electrical defibrillation, including cardioversion, and more specifically to the structure for an electrode used in implantable defibrillation systems. The term "defibrillation", as used herein, includes cardioversion which is another relatively high energy delivery system, as compared with pacing.

The principal object of this invention is to lower the defibrillation energy of a defibrillation electrode by overcoming the above problems regarding the size of the electrode while still providing a large surface area of contact, thereby maintaining a low impedance at the heart-electrode interface for obtaining maximum efficiency of energy delivered to the heart. Specifically, it is the primary goal of the present invention to provide as large an active discharge area as possible in as small a planar package as possible.

Another object of this invention is to provide a relatively low energy defibrillation electrode that facilitates adequate current distribution while avoiding the risk of an electrical short-circuit or a low impedance shunt developing between two opposing electrodes.

The present invention comprises a low energy defibrillation electrode having a novel structure to increase the surface area of contact on the heart by maximizing electrode-body fluid contact while still keeping the overall dimensions of the electrode small. By keeping the electrode smaller in size without sacrificing electrode-body fluid contact, less energy input is required for defibrillation and the risk of developing an electrical short between an opposing discharge electrode is also reduced.

In one preferred embodiment, the electrode is formed into a patch comprising a plurality of stacked screens of conductive titanium, platinum, platinum-iridium, or other similar mesh screen attached to an insulation layer on the surface of the electrode facing away from the heart. The mesh is formed of woven titanium filaments having natural pores developed from the weaving process. The filaments used to fabricate the mesh screens may have round, square or rectangular cross sections. The pores allow body fluids to flow between layers to form a pool of conductive blood. Therefore, the effective surface area of body fluid contact and thus tissue contact is greatly increased without covering a large surface area of the heart. In another preferred embodiment, having found that highly-efficient discharges are possible, the electrode of one or a plurality of layers is formed without insulation facing away from the direction of discharge.

Another object of the present invention is to increase the surface area of contact of the electrode further by etching grooves in or roughening the surface of the titanium mesh layer that faces the heart, or of each of the titanium mesh layers.

It is yet another object of this invention to provide for repositioning of a patch electrode by preventing tissue in-growth into the porous mesh through the use of polymeric materials such as hydrogels.

It is a further object of this invention to aid in the treatment or stabilization of certain cardiac arrhythmias by the elution of various drugs from the surfaces of the electrode.

The manner in which these and other objects are accomplished will become more readily apparent when reference is made to the following description, taken in conjunction with the accompanying drawings.

DETAILED DESCRIPTION OF THE INVENTION

Figure 1:
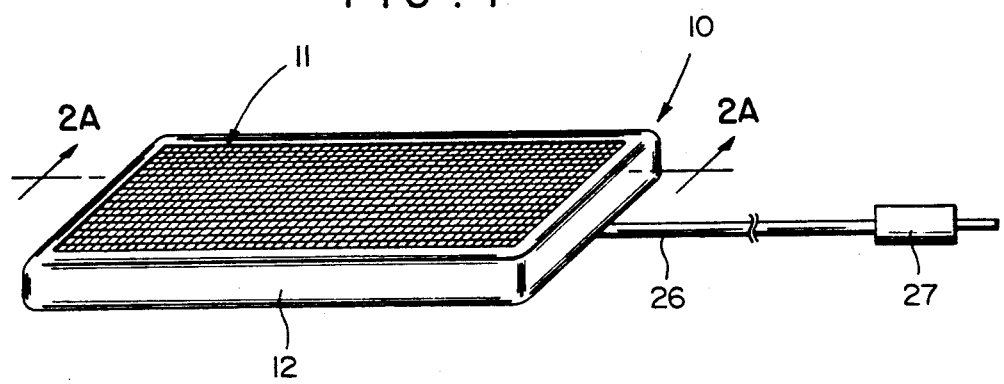
FIG. 1 is a perspective view of the electrode of the present invention.
Figure 2A:
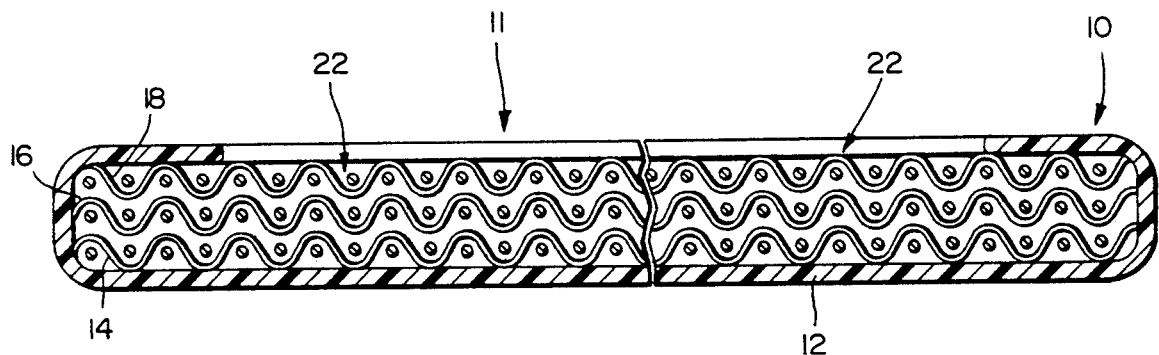
FIG. 2A is a cross-sectional view taken through line 2—2 of FIG. 1.

Referring first to FIGS. 1 and 2A, the inventive electrode 10 is shown including a discharge volume region 11 comprised of conductive mesh screens 14, 16, and 18 confined by an insulation element 12. Insulation element 12 occupies the surface of the electrode facing away from the heart and wraps over the edge of region 11. The conductive mesh screens 14, 16, and 18 overlie one another and are tied together electrically though they may be physically separated slightly. To augment the conductivity of the screens, the screens can also be electrically connected together proximate the connection of lead 26 to the electrode 10. Lead 26 includes a plug 27 for connecting electrode to a source of electrical energy within the defibrillator unit as is known in the art. The conductive mesh screens 14, 16, and 18 could also be comprised of a bundle conductive wires or coiled ribbon.

In the preferred embodiment, each conductive screen 14, 16, and 18 is formed of titanium, platium, or platium-iridium mesh having pores developed naturally between the transverse threads of the weaving process. The pores should be sized so as to permit the body fluids including tissue fluids, extra-cellular fluids such as pericardial fluids and blood flow therethrough. Because it is necessary to maximize surface contact area, the threads or wires of the conductive mesh should be as thin as possible for providing the appropriate size porers, but not so thin so as to avoid brittleness and mechanical fatigue. Typically, the diameter of the wires should be equal to the size of the pores.

While electrode 10 is shown having one large aperture defining discharge region 11, it is envisioned that transverse insulation elements can be provided across the aperture for creating a plurality of apertures.

Figure 2B:
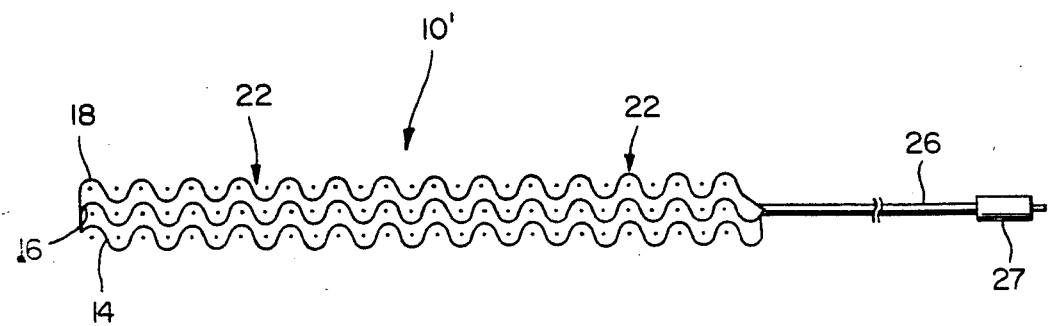
FIG. 2B is a cross-sectional view similar to FIG. 2A but illustrating a modified embodiment of the present invention.

A modified embodiment is illustrated in FIG. 2B. Electrode 10' is similar to electrode 10 without the insulative backing 12. Electrode 10' comprises only the screens 14, 16, and 18, and is used in the same way as electrode 10 as will be described in conjunction with FIG. 4. In addition, electrode 10' could be developed from but a single conductive layer.

To further increase the contact area, a conductive screen can be etched or otherwise miscrospically textured to create pits or indentations 22 shown in FIGS. 2A and 2B. While this is shown only on screen 18, it is envisioned to create such indentations on all of the conductive screens.

Figure 3:
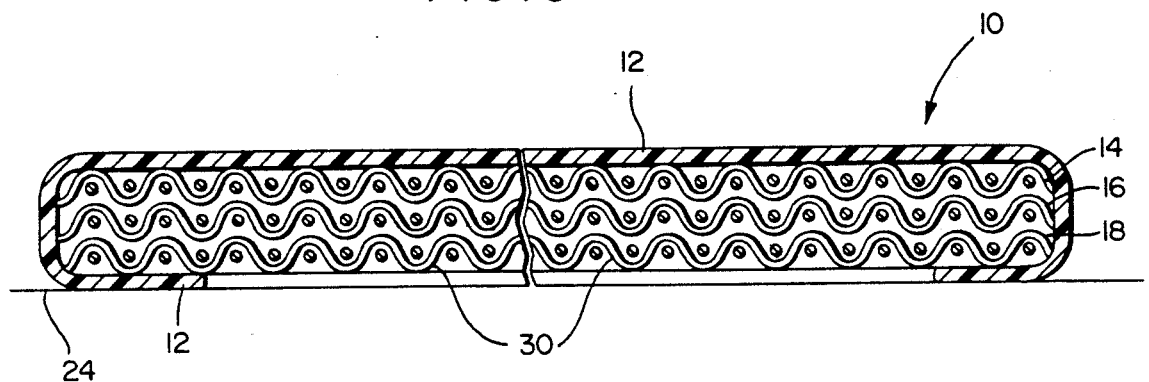
FIG. 3 is a cross-sectional view of the electrode of FIG. 1 mounted on the surface of a heart.

In operation, the electrode 10 is surgically attached to the surface of the heart 24 (or other body tissue, for example, subcutaneously). Typically, an electrolyte fluid is applied at the electrode-tissue interface as shown in FIG. 3. Due to the porous effect of the conductive mesh layers, body fluids on the surface of the heart 24 flow and through each porous conductive screen 14, 16, and 18. By allowing the flow of body fluids, the electrode-tissue interface is augmented by the electrolyte characteristics of the body fluids. The actual surface area of body fluid-electrode contact is much larger than with conventional flat electrodes. At the same time, because electrode 10 does not occupy as much planar or "foot print" area on the heart 24 as conventional flat electrodes, the risk of an electrical short developing between electrode 10 and another electrode of similar or other construction, is reduced. Moreover, the indentations 22 of the mesh screens further increase the area of body fluid-electrode contact which results in efficient energy delivery to the heart when the electrode is energized.

Although for some purposes, it is desirable for tissue to grow in and around implantable electrodes, such is undesirable for the electrode of the present invention. In the event that the electrode must be removed due to an infection at the implanted site, for example, tissue in-growth into the porous structure of the electrode will make the explanting of the electrode hazardous to the patient. Therefore, polymeric materials such as hydrogels 30 or other porous coverings (such as the DACRON TM cloth used for vein grafts) are incorporated in the porous structure to prevent tissue in-growth into the conductive mesh screens, thus allowing for easy explantation if necessary and for maintaining the porous nature of the electrode. These types of hydrogels are disclosed in a publication entitled "Biomedical Applications of Hydrogels, Review Critical Appraisal", by B. D. Ratner, published in "Biocompatibility of Clinical Implant Materials", Volume II, CRC Press, Boca Raton, 1981.

The hydrogel 30 can also serve as a drug reservoir for antibiotic, antiseptic, antiarrhythmic, antiinflammatory steriod or other agents. For example, to avoid the possibility of an infection developing at the implanted site, an antibiotic drug elution can be employed within the structure of the electrode 10. Furthermore, an antiarrhythmic drug can be employed to assist in converting abnormal heart rhythm to normal sinus rhythm. Alternatively, the antibiotic can be incorporated in the silicone backing material, or in the silicone surface of the lead 26.

Figure 4:
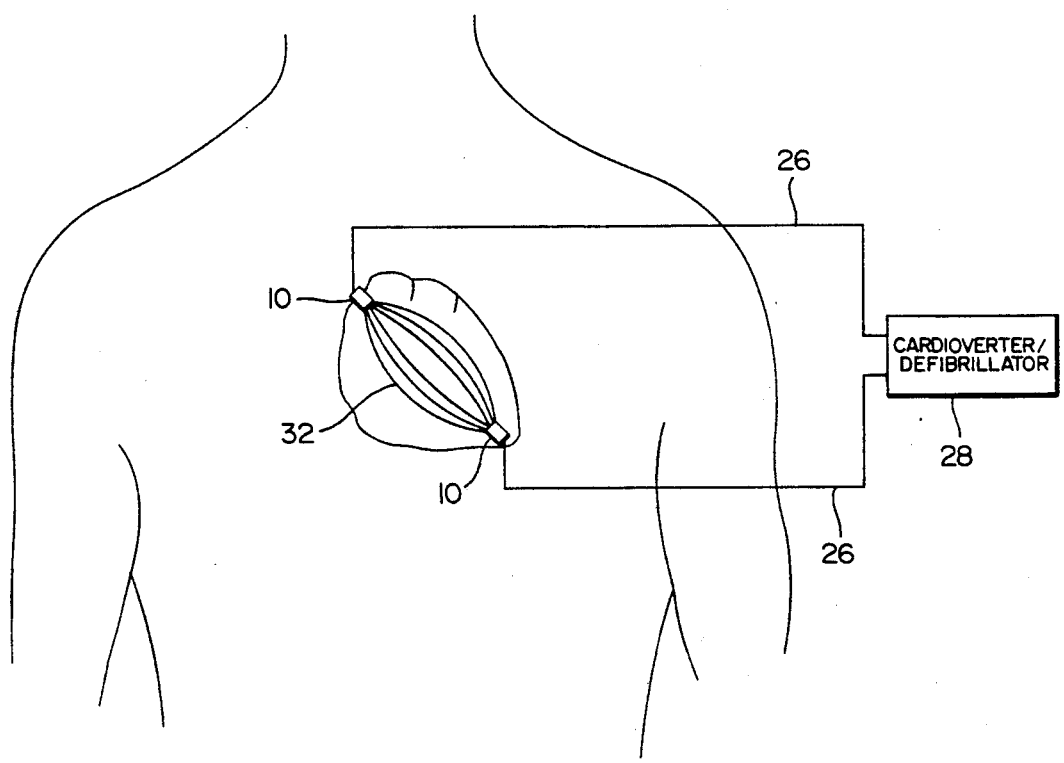
FIG. 4 is a schematic diagram of the electrode of the present invention used in a defibrillation system.

FIG. 4 shows the electrode 10 used in a defibrillation system. Two opposing electrodes, at least one of which being of the construction of electrode 10, are surgically attached to the heart and connected via leads 26 to an implanted cardioverter/defibrillator 28. When energy is applied to the electrodes, an electric field is created across the heart as shown by field lines 30.

Although shown in a generally rectangular shape, the shape and dimensions of the patch electrode 10 may vary. It is contemplated that the total thickness of the assembled electrode is on the order of 0.060", with the thickness of each conductive layer being on the order of 0.012". The surface area of the conductive portion of the electrode, facing the heart, is preferably 30 square centimeters. The pores defined by the weave of the titanium mesh are on the order of 0.006". Furthermore, while the electrode 10 has been disclosed as comprising three layers of conductive material, it should be understood that any number of conductive layers can be employed.

The defibrillation electrode structure of this invention provides maximum energy distribution to the heart while still keeping the actual surface area dimensions of the electrode small. As a result, the required energy input to produce adequate defibrillating electric fields on the heart is less than that required of previous defibrillation electrodes. To further reduce the required energy input, drug elution of a steroid can be used at the electrode tissue interface. Drug elution modifies the local tissue responses and cardiac activity.

It is understood that the above detailed description is intended by way of example only and is not intended to limit the present invention in any way, except as set forth in the following claims.

What is claimed is:

1. A defibrillation electrode of the type for implantation on or about the heart of a patient for connection to an implantable electrical defibrillation system, said electrode comprising:
   a conductive discharge volume region comprising at least two layers of porous electrically conductive screen, said at least two layers of porous electrically conductive screen substantially filling said conductive discharge volume region but allowing the flow of body fluids therethrough for making intimate electrical contact with the body fluids;
   an insulation element attached to said layers of conductive screen for occupying a surface of said electrode facing away from the heart.

2. The electrode of claim 1, wherein each of said conductive screens is formed of titanium mesh.

3. The electrode of claim 1, wherein each of said conductive screens is formed of platinum mesh.

4. The electrode of claim 1, wherein each of said conductive screens is defined by bundles of wires.

5. The electrode of claim 1, wherein each of said conductive screens is defined by woven conductive filaments.

6. The electrode of claim 1, wherein each of said conductive screens is defined by coiled conductive filaments.

7. The electrode of claim 1, wherein said insulation element is formed of silicone material.

8. The electrode of claim 1, wherein at least one of said conductive screens is microscopically textured for increasing the surface area of the conductive screen.

9. The electrode of claim 1, and further including a polymeric material incorporated in the porous conductive screens of said electrode for preventing tissue in-growth in said conductive discharge volume region of said electrode after implantation.

10. The electrode of claim 9, wherein said polymeric material is a hydrogel material.

11. The electrode of claim 10, and further comprising an antibiotic agent incorporated in the hydrogel material for treating device infection.

12. The electrode of claim 10, and further comprising an antiarrhythmic agent incorporated in the hydrogel material for treating device infection.

13. The electrode of claim 9, and further comprising an antibiotic agent incorporated in the polymeric material for treating device infection.

14. The electrode of claim 9, and further comprising an antiarrhythmic agent incorporated in said polymeric material.

15. The electrode of claim 1, and further comprising an antibiotic agent incorporated in the insulation element for treating infection.

16. A defibrillation electrode of the type for implantation on or about the heart of a patient for connection to an electrical defibrillation system, said electrode comprising:
- a conductive discharge volume region comprising at least two layers of porous electrically conductive screen, said at least two layers of porous electrically conductive screen filling said conductive discharge volume region entirely but allowing the flow of body fluids therethrough for making intimate electrical contact with the body fluids; and
- said at least two layers being disposed substantially parallel to each other and substantially parallel to a reference plane passing through said conductive discharge volume region.

17. The electrode of claim 16, wherein each of said conductive screens is formed of titanium mesh.

18. The electrode of claim 16, wherein each of said conductive screens is formed of platinum mesh.

19. The electrode of claim 16, wherein each of said conductive screens is defined by bundles of wires.

20. The electrode of claim 16, wherein each of said conductive screens is defined by woven conductive filaments.

21. The electrode of claim 16, wherein each of said conductive screens is defined by coiled conductive filaments.

22. The electrode of claim 16, wherein at least one of said conductive screens is microscopically textured for increasing the surface area of the conductive screen.

23. The electrode of claim 16, and further including a polymeric material incorporated in the porous conductive screens of said electrode for preventing tissue ingrowth in said conductive discharge volume region of said electrode after implantation.

24. The electrode of claim 23, wherein said polymeric material is a hydrogel material.

25. The electrode of claim 24, and further comprising an antibiotic agent incorporated in the hydrogel material for treating device infection.

26. The electrode of claim 24, and further comprising an antiarrhythmic agent incorporated in the hydrogel material for treating device infection.

27. The electrode of claim 23, and further comprising an antibiotic agent incorporated in said conductive screens by means of said polymeric material for treating device infection.

28. The electrode of claims 23, and further comprising an antiarrhythmic agent incorporated in the polymeric material.

29. An electrode of the type for implantation on or about the heart of a patient for connection to an electrical defibrillation system, said electrode comprising:
- a conductive discharge volume region comprising at least two layers of porous electrically conductive screen, said at least two layers of porous electrically conductive screen filling said conductive discharge volume region entirely but allowing the flow of body fluids therethrough for making intimate electrical contact with the body fluids, said discharge volume region having a first conductive surface facing towards the heart and a second conductive surface facing away from the heart, both of said conductive surfaces for being exposed to body tissue without being insulated therefrom.

30. The electrode of claim 29, wherein said electrically conductive screen is titanium mesh.

31. The electrode of claim 29, wherein said electrically conductive screen is platinum mesh.

32. The electrode of claim 29, wherein said electrically conductive screen is a bundle of wires.

33. The electrode of claim 29, wherein said electrically conductive screen is woven conductive filaments.

34. The electrode of claim 29, wherein said electrically conductive screen is coil conductive filaments.

35. The electrode of claim 29, and further comprising a polymeric material incorporated in said conductive screen and an antiarrhythmic agent incorporated in said polymeric material.

36. The electrode of claim 35, wherein said polymeric material is a hydrogel material.

37. The electrode of claim 29, and further comprising a polymeric material incorporated in said conductive screen and an antibiotic agent incorporated in said polymeric material.

38. The electrode of claim 37, wherein said polymeric material is a hydrogel material.

* * * * *